United States Patent
Hisamatsu et al.

(10) Patent No.: US 8,043,279 B2
(45) Date of Patent: Oct. 25, 2011

(54) CATHETER AND MEDICAL TUBE

(75) Inventors: Takatomo Hisamatsu, Tokyo (JP);
Katsuaki Soma, Fujinomiya (JP);
Masaki Sekino, Fujinomiya (JP);
Junichi Kobayashi, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1050 days.

(21) Appl. No.: 10/603,664

(22) Filed: Jun. 26, 2003

(65) Prior Publication Data
US 2004/0059292 A1    Mar. 25, 2004

(30) Foreign Application Priority Data
Jun. 26, 2002   (JP) ................. 2002-186603

(51) Int. Cl.
*A61M 25/00*    (2006.01)
*A61M 29/00*    (2006.01)
(52) U.S. Cl. ........................ 604/525; 606/194
(58) Field of Classification Search ................. 606/194; 604/525, 264, 524, 526, 103.09
See application file for complete search history.

(56) References Cited

U.S. PATENT DOCUMENTS

| | | | |
|---|---|---|---|
| 5,125,909 A * | 6/1992 | Heimberger | 604/264 |
| 5,207,482 A * | 5/1993 | Hart et al. | 303/33 |
| 5,217,482 A * | 6/1993 | Keith | 606/194 |
| 5,328,472 A | 7/1994 | Steinke et al. | |
| 5,531,719 A | 7/1996 | Takahashi | |
| 5,545,132 A | 8/1996 | Fagan et al. | |
| 5,807,354 A | 9/1998 | Kenda | |
| 5,911,715 A * | 6/1999 | Berg et al. | 604/525 |
| 6,036,670 A * | 3/2000 | Wijeratne et al. | 604/96.01 |
| 6,375,774 B1 | 4/2002 | Lunn et al. | |
| 2002/0177800 A1 | 11/2002 | Bagaoisan et al. | |

FOREIGN PATENT DOCUMENTS

| | | |
|---|---|---|
| EP | 1 103 281 A2 | 5/2001 |
| JP | 7-308383 A | 11/1975 |
| JP | 6-277296 A | 10/1994 |
| JP | 7-308383 | 11/1995 |
| JP | 2000-126301 A | 5/2000 |
| JP | 2000-197704 | 7/2000 |
| JP | 2000-254235 | 9/2000 |
| WO | WO 93/04722 A2 | 3/1993 |

* cited by examiner

*Primary Examiner* — Corrine M McDermott
*Assistant Examiner* — Melissa Ryckman
(74) *Attorney, Agent, or Firm* — Buchanan Ingersoll & Rooney PC

(57) ABSTRACT

A catheter includes a proximal shaft having a relatively high rigidity, a distal shaft provided on a front portion of the proximal shaft so as to be in fluid communication with proximal shaft and having a rigidity lower than that of the proximal shaft, a hub mounted to the vicinity of a rear end of the proximal shaft and configured to allow a pressure applying apparatus to be mounted to the hub, and a balloon provided on a front portion of the distal shaft so as to be in fluid communication with the distal shaft and configured to receive pressure applied from the hub. The catheter also includes a guide wire lumen. In this catheter, at least a front portion of the distal shaft is configured as a grooved portion having a groove or grooves.

11 Claims, 7 Drawing Sheets

CATHETER AND MEDICAL TUBE

BACKGROUND OF THE INVENTION

The present invention relates to a diagnostic or therapeutic catheter for performing various treatments in blood vessels and a medical tube used for endoscopes and the like. In particular, the present invention relates to a dilatation balloon catheter used for treating a stricture generated in a lumen such as a blood vessel by dilating the stricture, thereby improving the flow of blood in a peripheral side of the stricture, and a living organ dilatation catheter capable of delivering a living organ dilatation stent to a target living organ cite with a safety and a smooth operationality.

In recent years, functions of medical tubes have been significantly enhanced. Examples of such high function medical tubes include a vasodilatation balloon catheter used for percutaneous transluminal angioplasty for dilating a stricture in a blood vessel; a living organ dilatation catheter capable of delivering a living organ dilatation stent to a target living organ cite with a safety and a smooth operationality; a cerebrovascular catheter for injecting an embolizing material or a coil in an aneurysm or arteriovenous malformation caused in a cerebral blood vessel; an ultrasonic catheter capable of performing accurate observation or diagnosis for the inside of a blood vessel using ultrasonic diagnostic equipment; and an endoscope capable of performing accurate observation or diagnosis for the inside of a blood vessel, a bile duct, or a pancreatic duct using an image diagnostic equipment.

Such a high function medical tube has been required to have not only durability but also operationality allowing the tube to be inserted in a fine, complicated blood vessel rapidly, highly selectively. Specific examples of these requirements include (1) "pushability" allowing a catheter to be easily pushed by an operator so as to be inserted in a blood vessel; (2) "trackability" allowing a catheter to be smoothly advanced in a complicated meandering blood vessel along a previously inserted guide wire without damaging the inner wall of the blood vessel; (3) "torque transmission performance" allowing a rotational force applied on the proximal side of a catheter tube to be certainly transmitted to the distal end; and (4) "kink resistance" capable of suppressing occurrence of kink upon handling of a catheter before treatment, upon pushing the catheter, and upon pulling off a guide wire. Examples of the requirements for the high function medical tubes further include (1) "low-profile characteristics" realized by making the outer diameter of the tube as fine as possible for thinning a guiding wire adapted to guide the catheter to a target cite in order to reduce the physical or mental burden of a patient or for reducing a friction resistance with the wall of a blood vessel; (2) "thin-wall characteristic" realized by sufficiently ensuring the lumen of the tube so as to keep good operationality of a guide wire; and (3) "flexibility of the front portion of the catheter" for reducing damage of the wall of a blood vessel caused by the front portion of the catheter.

In this way, the high function medical tube is required to have not only the fineness and torque transmission performance but also the incompatible characteristics such as hardness and softness, and thin wall and resistance against breaking. Also, the ultrasonic catheter must satisfy a requirement to partially harden the tube. To produce catheter tubes satisfying these requirements, various techniques have been developed.

For example, most of vasodilatation balloon catheters commercially available at present have a basic structure including a shaft main body including a balloon inflation lumen and a guide wire lumen, and a balloon provided at a front portion of the shaft main body, wherein the shaft main body has a distal portion having a relatively low rigidity and a proximal portion having a relatively high rigidity. According to these balloon catheters, in a rigidity transition region positioned between the distal portion and the proximal portion of the shaft main body, shaft portions having different rigidities are connected to each other or the outer diameter or wall thickness is changed in order to smoothly change the rigidity or to prevent occurrence of kink due to stress concentration when a sharp bending force is applied thereto.

In the case of connecting the shaft portions having different rigidities, however, it fails to obtain a smooth change in rigidity, and therefore, there occurs a problem that stress is concentrated at the boundary (interface) of the connection portion, thereby tending to cause kink.

Also, there occurs a problem that in the case of advancing a vasodilatation balloon catheter along a meandering blood vessel to a stricture generated in a peripheral vascular vessel such as a coronary artery, kink is liable to occur at a front portion, adjacent to the balloon, of the shaft main body. The occurrence of such kink makes it difficult to smoothly transmit a pushing force given at the proximal end of the catheter to the distal end of the catheter and hence to push the catheter to a more peripheral vascular vessel.

To smoothly change the rigidity at the front portion, adjacent to the balloon, of a shaft main body for preventing occurrence of kink, some of commercially available vasodilatation balloon catheters are configured to gradually reduce the outer diameter or wall thickness of the front portion of the shaft main body in the direction toward the distal end. However, since the shaft is generally produced by extrusion molding, there arises a problem that an extrusion speed upon extrusion from a die, an extruded amount of a resin material, and the like must be accurately controlled to change the outer diameter or wall thickness of the shaft by extrusion molding, and therefore, the skillful technique is required for production of the shaft. Additionally, in the case of preventing occurrence of kink only by changing the outer diameter or wall thickness of the shaft, the effect of preventing occurrence of kink has a limitation.

SUMMARY OF THE INVENTION

An object of the present invention is to provide a fine catheter and a fine medical tube, each of which is excellent in torque transmission performance and kink resistance as well as pushability, trackability, and flexibility of the front portion, wherein the catheter and the medical tube can be produced by a simple production process. A specific object of the present invention is to provide a balloon catheter capable of suppressing occurrence of kink in a front portion, adjacent to a balloon, of a shaft main body, thereby reaching a living lumen such as a more peripheral vascular vessel.

To achieve the above object, according to a first aspect of the present invention, there is provided a catheter including a proximal shaft; a distal shaft connected to a front portion of the proximal shaft; a hub provided to the rear side of the proximal shaft; a balloon provided at a front portion of the distal shaft; a balloon lumen for communicating the hub to the inside of the balloon; and a guide wire lumen for allowing a guide wire to be inserted through the guide wire lumen, the guide wire lumen including a distal side aperture positioned on the distal side from a front end of the balloon and a proximal side aperture positioned on the rear side from a rear end of the balloon; wherein at least a front portion, positioned on the rear side from the balloon, of the distal shaft is configured as a grooved portion having a groove or grooves.

According to a second aspect of the present invention, there is provided a catheter including a proximal shaft having a high rigidity; a distal shaft provided on a front portion of the proximal shaft so as to be in fluid communication with the proximal shaft and having a rigidity lower than that of the proximal shaft; a hub connected to the vicinity of a rear end of the proximal shaft and configured to allow a pressure applying apparatus to be connected to the hub; a balloon provided on a front portion of the distal shaft so as to be in fluid communication with the distal shaft and configured to receive pressure applied from the hub; and a guide wire lumen for allowing a guide wire to be inserted through the guide wire lumen, the guide wire lumen including a distal side aperture positioned on the distal side from a front end of the balloon and a proximal side aperture positioned on the rear side from a rear end of the balloon; wherein at least a front portion of the distal shaft is configured as a grooved portion having a groove or grooves.

According to a third aspect of the present invention, there is provided a medical tube including a tube-like shaft; and a lumen formed in the shaft; wherein the shaft includes a groove or grooves formed with their depths changed in the direction toward a distal end of the medical tube.

The catheter of the present invention having the above-described configuration is advantageous in being excellent in pushability, trackability, torque transmission performance, and kink resistance, and having flexibility at the front portion of the catheter, and is also advantageous in being capable of suppressing occurrence of kink, thereby reaching a more peripheral target cite of a living body because the distal shaft has no rapid change point of rigidity and exhibits the rigidity (physical property) smoothly changed in the longitudinal direction. In particular, the balloon catheter of the present invention is advantageous in being capable of suppressing occurrence of kink in a front portion, adjacent to a balloon, of a shaft main body, thereby smoothly reaching a more peripheral vascular vessel or other living lumen.

The medical tube of the present invention having the above-described configuration is advantageous in being excellent in pushability, trackability, torque transmission performance, and kink resistance, and having a flexibility at the front portion of the tube-like shaft, and is also advantageous in being capable of suppressing occurrence of kink, thereby reaching a more peripheral target cite of a living body because the tube-like shaft has no rapid change point of rigidity and exhibits the rigidity (physical property) smoothly changed in the longitudinal direction.

The catheter and the medical tube of the present invention have a further advantage that since the rigidity (physical property) can be more smoothly changed by changing the pitch or depth of a groove or grooves in the longitudinal direction of a grooved portion or combining the changes in pitch and depth of the groove or grooves with each other, each of the catheter and the medical tube is capable of significantly suppressing occurrence of kink, thereby easily reaching a more peripheral vascular vessel or other living lumen.

In addition, according to the present invention, the steps of producing each of the catheter and the medical tube are simpler than the prior art steps of connecting shafts having different rigidities or changing the wall thickness or outer diameter of the shaft by extrusion molding.

BRIEF DESCRIPTION OF THE DRAWINGS

These and other objects, features, and advantages of the present invention will be described in more detail with reference to the accompanying drawings, wherein.

DETAILED DESCRIPTION OF THE PREFERRED EMBODIMENTS

A catheter and a medical tube according to the present invention will be hereinafter described with reference to the drawings.

Figure 1:
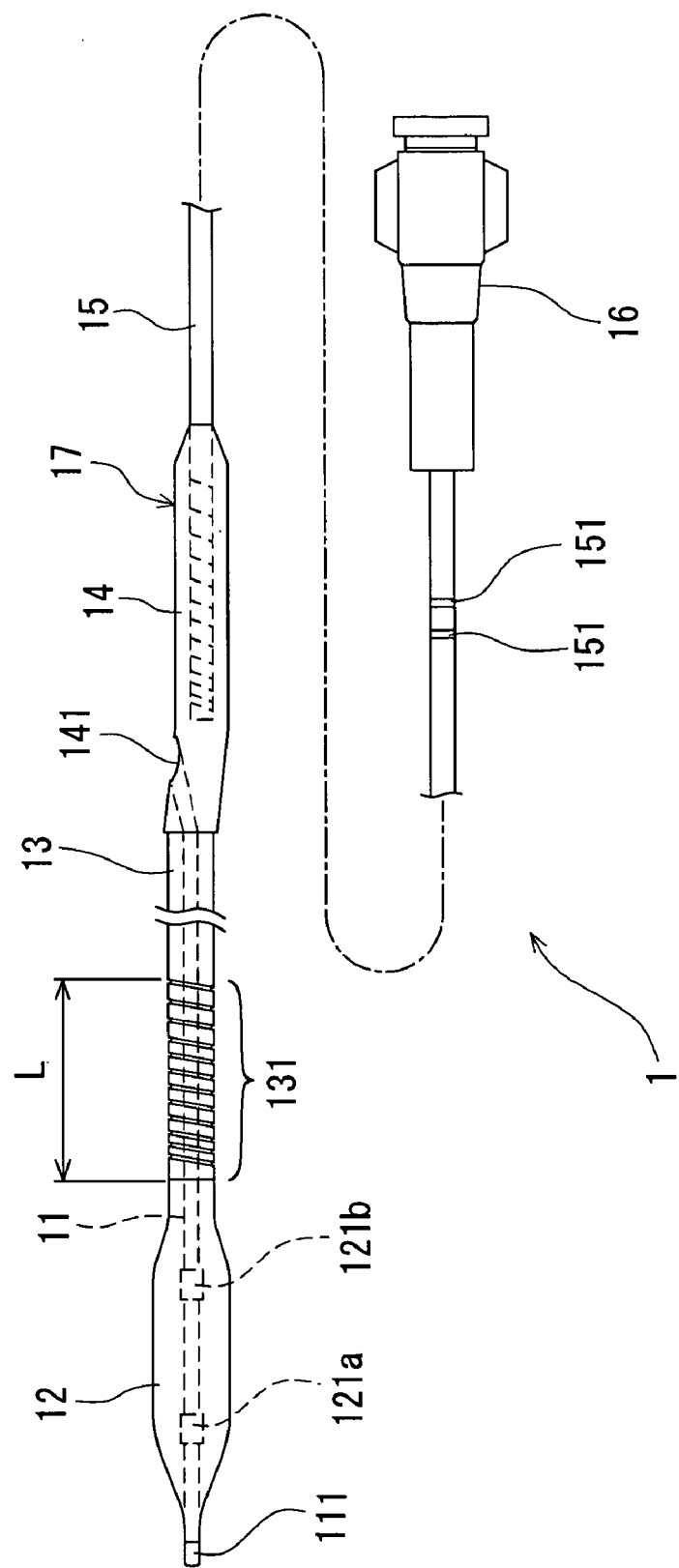
FIG. 1 is an enlarged front view of one embodiment of a catheter (medical tube), with parts partially omitted.
Figure 2:
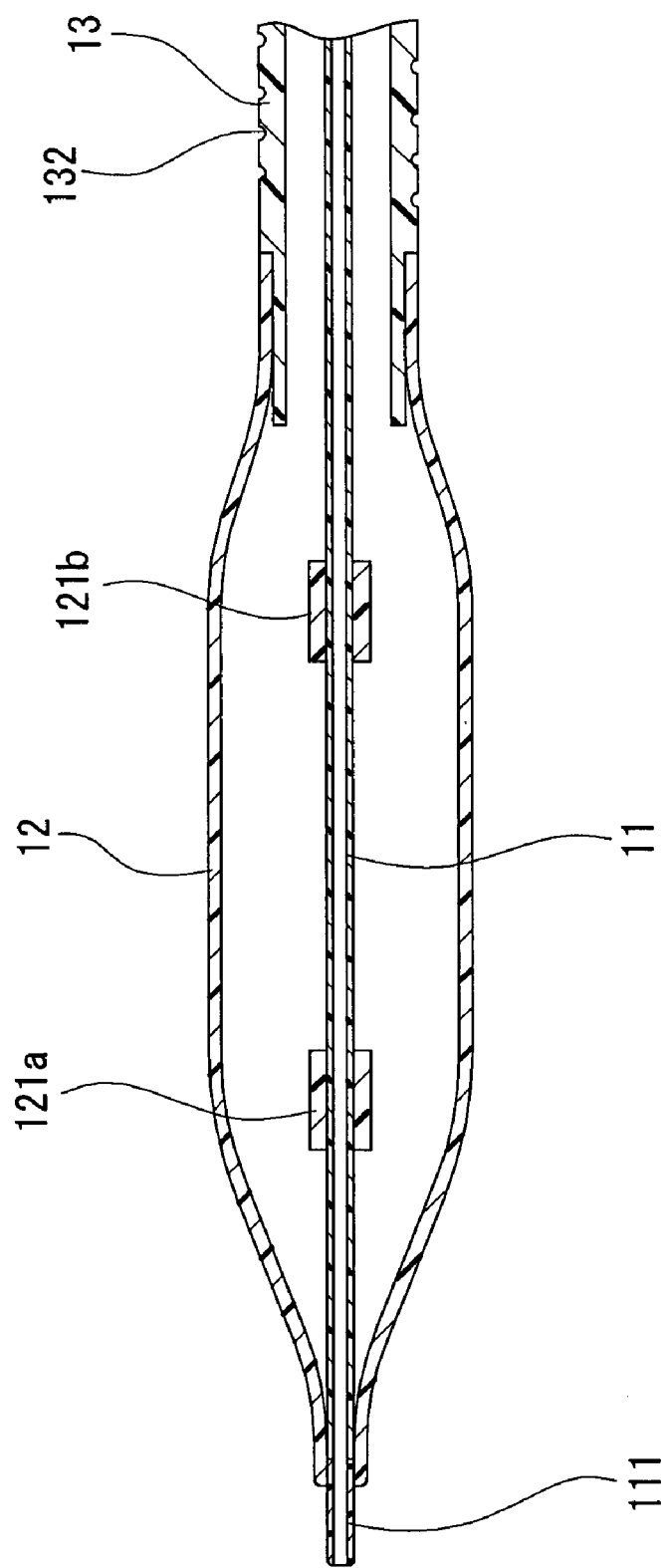
FIG. 2 is an enlarged sectional view of a front side portion of the catheter shown in FIG. 1.
Figure 3:
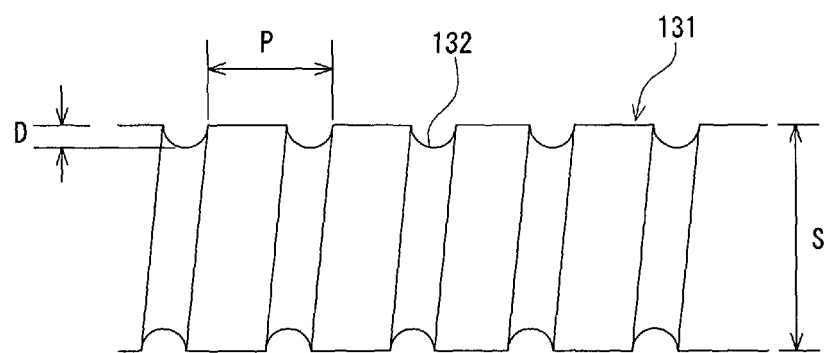
FIG. 3 is an enlarged appearance view of a grooved portion of the catheter shown in FIG. 1.
Figure 4:
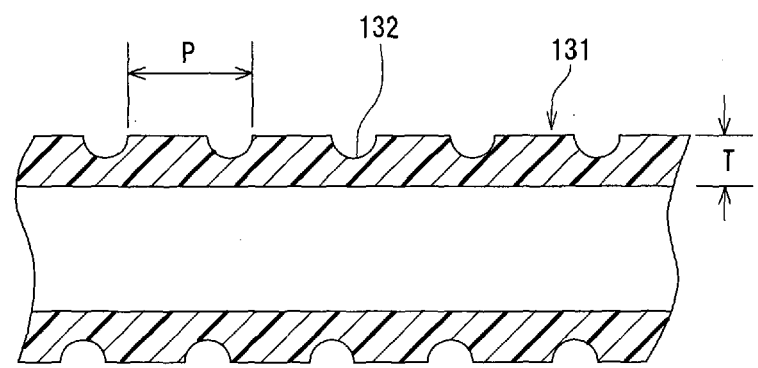
FIG. 4 is an enlarged sectional view of the grooved portion of the catheter shown in FIG. 1.
Figure 5:
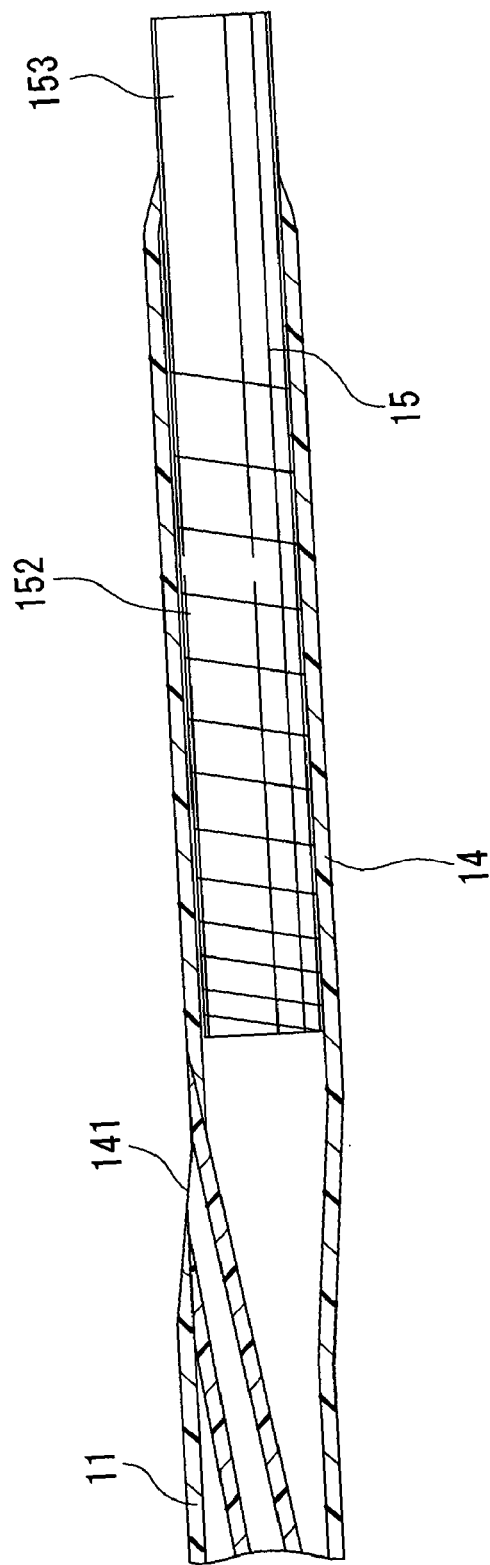
FIG. 5 is an enlarged sectional view showing an intermediate portion, a front portion of a proximal shaft, and a rear portion of a distal shaft of the catheter shown in FIG. 1.

FIG. 1 is an enlarged front view of one embodiment of a catheter (medical tube) of the present invention, with parts partially omitted; FIG. 2 is an enlarged sectional view of a front side portion of the catheter shown in FIG. 1; FIG. 3 is an enlarged appearance view of a grooved portion of the catheter shown in FIG. 1; FIG. 4 is an enlarged sectional view of the grooved portion of the catheter shown in FIG. 1; and FIG. 5 is a sectional view showing an intermediate section, a front portion of a proximal shaft, and a rear portion of a distal shaft of the catheter shown in FIG. 1. In these figures, the right side is taken as the proximal side, and the left side is taken as the distal side.

In this embodiment, a catheter according to a first feature of the present invention is embodied by a catheter 1 including a proximal tube-like shaft 15, a distal tube-like shaft 13 connected to a front portion of the proximal shaft 15, a hub 16 connected to the rear side of the proximal shaft 15, a balloon 12 provided at a front portion of the distal shaft 13, a balloon lumen for communicating the hub 16 to the inside of the balloon 12, and a guide wire lumen for allowing a guide wire to be inserted through the guide wire lumen, the guide wire lumen including a distal side aperture positioned on the distal side from a front end of the balloon 12 and a proximal side aperture positioned on the rear side from a rear end of the balloon 12. In this catheter, at least a front portion, positioned on the rear side from the balloon 12, of the distal shaft 13 is configured as a grooved portion 131 having a groove 132 or grooves.

A catheter according to a second feature of the present invention is embodied by a catheter 1 including a proximal shaft 15 having a relatively high rigidity, a distal shaft 13 provided on a front portion of the proximal shaft 15 so as to be in fluid communication with the proximal shaft 15 and having a rigidity lower than that of the proximal shaft 15, a hub 16 connected to the vicinity of a rear end of the proximal shaft 15 and configured to allow a pressure applying apparatus to be connected to the hub 16, a balloon 12 provided on a front side of the distal shaft 13 so as to be in fluid communication with the distal shaft 13 and configured to receive pressure applied from the hub 16, and a guide wire lumen for allowing a guide wire to be inserted through the guide wire lumen, the guide wire lumen including a distal side aperture positioned on the front side from a front end of the balloon 12 and a proximal side aperture 141 positioned on the rear side from a rear end of the balloon 12. In this catheter, at least a front portion of the distal shaft 13 is configured as a grooved portion 131 having a groove 132.

The distal shaft 13 of the above catheters may has a distal portion and a proximal portion, and the rigidity of the proximal portion of the distal shaft is lower than that of the proximal shaft and is higher than that of the distal portion of the distal shaft.

A medical tube according to a third feature of the present invention is embodied by a medical tube including a tube-like shaft (outer tube shaft) 17 and a lumen formed in the outer tube shaft 17, wherein the outer tube shaft 17 includes a groove or grooves 132 formed with their depths changed in the direction toward a distal end of the medical tube. The medical tube of the present invention is usable for catheters, endoscopes, and the like.

As shown in FIG. 1, a catheter 1 is a so-called rapid exchange type dilatation balloon catheter to be inserted into a blood vessel along a guide wire (not shown). The catheter 1 includes a hub 16, an outer tube shaft 17, a balloon 12, and an inner tube shaft 11, which are arranged in this order from the proximal side of the catheter 1. The outer tube shaft 17 includes a proximal shaft 15, an intermediate section 14 (rear portion of a distal shaft), and a distal shaft 13, which are arranged in this order from the proximal side of the outer tube shaft 17.

A lure taper portion is formed on the hub 16 on the proximal side so as to allow a pressure applying apparatus such as an inflator to be connected to the hub 16 via the lure taper portion. The proximal shaft 15 made from a material having a relatively high rigidity such as a metal or a hard resin is connected to the hub 16 so as to be in fluid communication with the hub 16, that is, so as to allow liquid injected in the hub 16 to flow in the proximal shaft 15. The proximal shaft 15 is provided with a depth marker 151 for easily checking the depth of the catheter 1 inserted in a guiding catheter (not shown) during angioplasty. As will be fully described later, a front portion of the proximal shaft 15 is configured as a proximal shaft insertion portion 152.

The intermediate section 14 is connected to the front side of the proximal shaft 15 so as to be in fluid communication with the proximal shaft 15. In other words, the intermediate section (which is hereinafter often called "intermediate member") 14 for forming a rear portion of the distal shaft 13 is provided on the rear side of the distal shaft 13. Specifically, the front portion of the proximal shaft 15 is mounted to the intermediate member 14 having a rigidity lower than that of the proximal shaft 15 so as to allow liquid injected in the proximal shaft 15 to flow in the intermediate member 14. More specifically, the distal shaft (distal shaft main body) 13 having a relatively low rigidity, for example, made from a resin is provided on the distal side of the intermediate section (intermediate member) 14 for forming the rear portion of the distal shaft 13 so as to be in fluid communication with the intermediate member 14. A rear portion of the balloon 12 is provided on the front portion of the distal shaft 13 so as to be in fluid communication with the distal shaft 13. The balloon 12 provided on the front portion of the distal shaft 13 allows liquid having flown in the distal shaft 13 to flow in the balloon 12.

As shown in FIGS. 1 and 2, an inner tube shaft (or an inner tube) 11 coaxially extends through the distal shaft 13 and the balloon 12. The distal end of the inner shaft 11 forms a distal tip 111. The distal tip 111 extends outwardly from the front end of the balloon 12 and is liquid-tightly connected to the front side of the balloon 12. To be more specific, in this embodiment, the distal tip 111 is formed by a separate member fixed to the distal end of the inner tube shaft 11. The front portion of the balloon 12 is fixed so as to cover a connection portion between the tip 111 and the inner tube shaft 11. In addition, the distal tip 111 projects from the balloon 12.

On the other hand, the rear end of the inner shaft 11 extends to a guide wire aperture 141 formed in a portion located in a range from the intermediate section 14 to the distal shaft 13, and is liquid-tightly connected to the guide wire aperture 141. As shown in FIGS. 1, 2 and 5, the inner tube shaft 11 extends through the distal shaft 13 and reaches the intermediate member 14, and the distal end of the inner tube shaft 11 is fixed to the guide wire aperture 141 formed in the side surface of the intermediate member 14. A guide wire (not shown) is inserted in the inner tube shaft 11. In this case, the distal aperture of the distal tip 111 is taken as an inlet and the guide wire aperture 141 is taken as an outlet. The lumen of the inner tube shaft 11 and the lumen of the tip 111 form a guide wire lumen. As shown in FIGS. 1 and 2, radiopaque markers 121a and 121b are provided at inner positions, located around the inner shaft 11, of the balloon 12.

In a state that the balloon 12 is not inflated, the balloon 12 remains folded around the outer periphery of the inner tube shaft 11. In a state that the balloon 12 is inflated, a central portion of the balloon 12 becomes a nearly cylindrical shape, which allows easy dilatation of a stricture of a blood vessel. It is to be noted that the central portion of the balloon 12 is not necessarily formed into a completely cylindrical shape but may be formed into a polygonal cylindrical shape. The radiopaque markers 121a and 121b are provided to facilitate the positioning of the balloon 12 at a stricture cite under fluoroscopy during angioplasty.

As shown in FIG. 5, the proximal shaft 15 includes a main shaft portion 153, and the proximal shaft insertion portion 152. The proximal shaft insertion portion 152 is formed by spirally slitting the front portion of the proximal shaft 15 (or the front portion of the main shaft portion 153). In the example shown in this figure, the pitch of the spiral slit is short on the distal side of the slit and is long on the proximal side of the slit, and in an intermediate portion between the distal side and the proximal side of the slit, the pitch of the slit becomes gradually shorter toward the distal end. Accordingly, the pitch of the spiral slit becomes narrower toward the distal end. The proximal shaft insertion portion 152 is formed by spirally slitting the front portion of the main shaft portion 153 by laser cutting. According to the present invention, the configuration of making the pitch of the spiral slit narrower toward the distal end is not limited to that described above but may be realized by making the pitch of the spiral slit narrower toward the distal end at a constant rate from the proximal end to the distal end of the slit.

As shown in FIG. 5, the proximal shaft insertion portion 152 (that is, the front portion) of the proximal shaft 15 extends in the intermediate portion 14 to the vicinity of the guide wire aperture 141 provided in the intermediate portion 14. To be more specific, the proximal shaft insertion portion 152 is inserted from the proximal side of the intermediate portion 14 until the distal end thereof reaches the vicinity of the guide wire aperture 141. The rear portion of the inner tube shaft 11 is fixed to a portion (side port formed in the side surface) of the outer periphery of the intermediate portion 14. The proximal aperture of the inner tube shaft 11 is exposed to the outside of the intermediate portion 14, to form the guide wire aperture 141. The guide wire aperture 141 is not necessarily provided in the intermediate portion 14 but may be provided in either the proximal shaft 15 or the distal shaft 13. Alternatively, the guide wire aperture 141 may be provided at a boundary portion (connection portion) between the intermediate portion 14 and the distal shaft 13.

With such arrangement of the proximal shaft insertion portion 152 in the intermediate portion 14, it is possible to make the intermediate portion 14 lower in rigidity (that is, softer) than the main shaft portion 153 and higher in rigidity (that is, harder) than the distal shaft 13, and hence to gradually change the rigidity of the shafts forming the dilatation catheter 1 in the direction from the proximal side to the distal side. This is advantageous in preventing, even when the intermediate portion 14 is sharply curved, stress from being concentrated at one point, thereby reducing occurrence of kink.

In the catheter 1 configured as described above, when pressure is applied to the hub 16 by means of the pressure applying apparatus (not shown) connected to the hub 16, the pressure medium is transmitted from the hub 16 to the balloon 12 through the proximal shaft 15, the proximal shaft insertion portion 152, the intermediate portion 14, and a gap (lumen for inflation of the balloon 12) between the distal shaft 13 and the inner tube shaft 11, to dilate the balloon 12. It is to be noted that the proximal shaft 15, the intermediate portion 14, the distal shaft 13, the inner tube shaft 11, and respective connection portions each have a resistance against a pressure higher than a value causing burst of the balloon 12.

As shown in FIG. 1, the front portion of the distal shaft 13 (as part of the outer tube shaft 17) is configured as a grooved portion 131. To be more specific, the grooved portion 131 is formed in the front portion of the distal shaft 13, which portion is located on the rear (proximal) side from the connection portion between the distal shaft 13 and the balloon 12. As shown in FIGS. 3 and 4 on an enlarged scale, the grooved portion 131 has a groove 132. According to this embodiment, the groove 132 is formed into a spiral shape. The groove 132 extends in the longitudinal direction of the distal shaft 13, that is, the catheter 1. As a result of forming the groove 132, the grooved portion 131, that is, the front portion of the distal shaft 13 becomes softer than the rear portion, provided with no groove 132, of the distal shaft 13.

In this embodiment, the grooved portion 131 is provided in a region, adjacent to the balloon 12, of the outer tube shaft 17 (distal shaft 13). Accordingly, the rigidity of the catheter 1 is smoothly changed from the portion provided with the outer tube shaft 17 (distal shaft 13) containing the inner tube shaft 11 inserted therein to the portion provided with only the balloon 12 and the inner tube shaft 11, that is, provided with no outer tube shaft 17. As a result, even if the portion, adjacent to the balloon 12, of the outer tube shaft 17 (distal shaft 13) is sharply curved in a meandering portion of a blood vessel, it is possible to prevent stress from being concentrated at one point and hence to reduce occurrence of kink. This makes it possible to certainly transmit a pushing force applied on the proximal side of the catheter 1 to the distal end of the catheter 1, and hence to insert the catheter 1 to a more peripheral vascular vessel.

The spiral pitch (gap between adjacent turns of spiral) P of the groove 132 is not particularly limited, but from the viewpoint of making the grooved portion 131 sufficiently soft while ensuring a suitable strength of the grooved portion 131, the spiral pitch P may be set in a range of, preferably, about 5 to 40%, more preferably, about 10 to 30% of an outer diameter S of the distal shaft 13.

The pitch of the spiral groove 132 may be constant over the whole length of the grooved portion 131; however, as shown in FIG. 1, the pitch of the spiral grooves 132 is preferably changed so as to be short on the distal side of the grooved portion 131 and long on the proximal side of the grooved portion 131. With such a change in pitch, the grooved portion 131 becomes softer toward the distal side, to prevent rapid change in physical properties of the grooved portion 131, thereby allowing the boundary between the grooved portion and a non-grooved portion to be smoothly curved. This is advantageous in improving the operationality of the catheter 1. More preferably, the pitch of the groove 132 is changed so as to be short on the front portion of the grooved portion 131 and become gradually longer therefrom toward the proximal end of the grooved portion 131. With such a change in pitch, since the grooved portion 131 becomes gradually softer in the direction toward the distal end, the grooved portion 131 can be more smoothly curved. This is advantageous in further improving the operationality of the catheter 1.

In the case of changing the pitch of the groove 132, preferably, the pitch of the spiral groove 132 in the front portion (having the groove 132 arranged with a small pitch) of the grooved portion 131 is in a range of about 100 to 200 μm, and the pitch of the groove 132 in the rear portion (having the groove 132 arranged with a large pitch) of the grooved portion 131 is in a range of about 200 to 400 μm. In particular, in the intermediate portion between the front portion and the rear portion of the grooved portion 131, the pitch of the groove 132 is preferably set to be intermediate between the pitches on the distal and proximal sides or to be gradually changed. As long as the pitches of the groove 132 and the lengths of the front and rear portions of the grooved portion 131 are within the above-described ranges, the grooved portion 131 are sufficiently soft, and is not kinked during use of the catheter 1. In the catheter 1 shown in FIG. 1, the groove is formed by one spiral; however, they may be formed by two or more spirals. With respect to the spiral configuration, the gradual change in pitch of the groove 132 as shown in FIG. 1 is particularly preferred. In this spiral configuration, the front portion of the grooved portion 131 is very soft because of the narrow pitch of the spiral groove 132, and is therefore excellent in flexibility of the front portion of the catheter and trackability of the catheter, whereas the rear portion of the grooved portion 131 keeps a high hardness necessary for the catheter because of the wide pitch of the spiral groove or formation of no spiral grooves, and is therefore excellent in pushability of the catheter.

A depth D of the groove 132 shown in FIGS. 2 and 3 is not particularly limited, but from the viewpoint of making the grooved portion 131 sufficiently soft and ensuring a suitable strength of the grooved portion 131, the depth D may be in a range of, preferably, about 30 to 90%, more preferably, about 40 to 70% of a wall thickness T of the distal shaft 13. It is to be noted that the wall thickness T of the distal shaft 13 is measured as the wall thickness of a non-grooved portion, adjacent to the groove 132, of the distal shaft 13.

Figure 6:
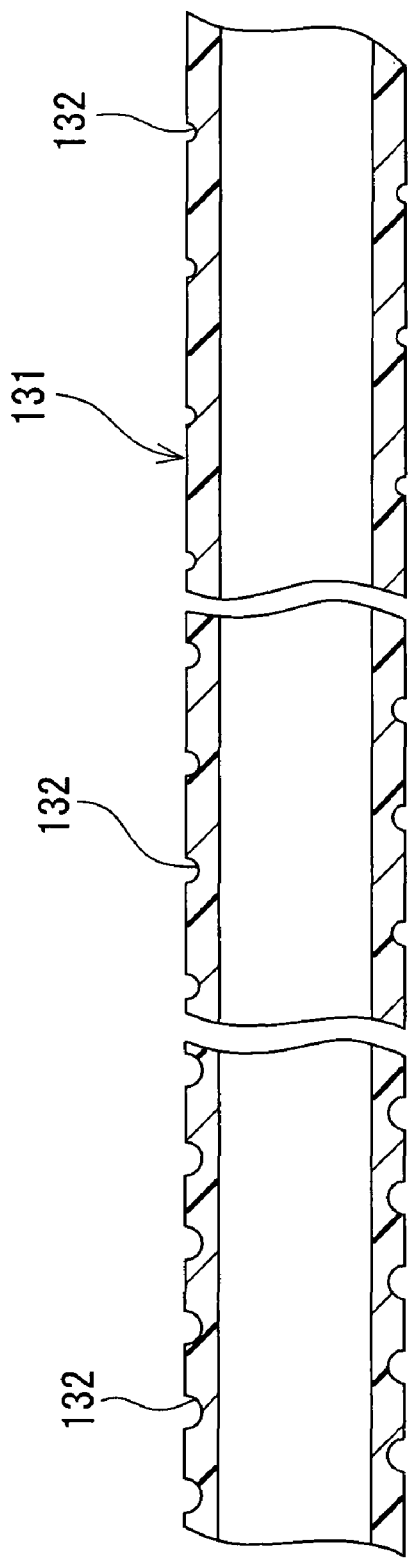
FIG. 6 is an enlarged sectional view of the grooved portion of the catheter shown in FIG. 1.

According to the present invention, the depth of the groove 132 may be constant over the whole length of the grooved portion 131, but is preferably changed in the direction toward the distal end of the catheter 1. With such a change of the depth, the rigidity of the catheter 1 can be more smoothly changed. As shown in FIG. 6, the depth of the groove 132 may be changed so as to be large on the distal side of the grooved portion 131 and small on the proximal side of the grooved portion 131. With this configuration, the distal side of the grooved portion 131 can be made softer than the proximal side of the grooved portion 131. The depth of the groove 132 may be changed either continuously or stepwise in the direction toward the distal end of the catheter or the medical tube.

In particular, the grooved portion 131 in the catheter 1 shown in FIG. 1 may have, from the distal side thereof, a first region, a second region, and a third region, wherein the depth of the groove 132 may be set such that the depth of the second region is larger than that of the third region and the depth of the first region is larger than that of the second region. With this configuration, since the depth of the groove 132 is not sharply changed at each of the vicinities of the distal and proximal ends of the grooved portion 131, a change in rigidity between the grooved portion 131 and a non-grooved portion becomes smooth, to thereby prevent occurrence of kink thereat. In particular, the change in rigidity of the catheter 1 becomes very smooth at a boundary between the portion provided with the outer tube shaft 17 (distal shaft 13) containing the inner tube shaft 11 inserted therein and the portion provided with only the balloon 12 and the inner tube shaft 11, that is, provided with no outer tube shaft 17, to thereby significantly effectively prevent occurrence of kink thereat.

In the case of changing the depth of the groove 132, the depth of the groove 132 in a portion having the deepest groove may be in a range of, preferably, about 30 to 90%, more preferably, 40 to 70% of the wall thickness T of the distal shaft 13. It is to be noted that the wall thickness T is measured as the wall thickness of a non-grooved portion, adjacent to the groove 132, of the distal shaft 13.

The length of the grooved portion 131 is not particularly limited, but from the viewpoint of suitable dispersion of stress, the length may be in a range of, preferably, about 10 to 80%, more preferably, 15 to 60% of the whole length of the distal shaft 13. In the example shown in FIG. 1, the grooved portion 131 is not provided on the rear portion of the distal shaft 13 but the present invention is not limited thereto. The grooved portion 131 may be formed over the whole length of the distal shaft 13 by suitably setting the pitch and the depth of the groove 132.

Materials, dimensions, and the like of respective members forming the catheter of the present invention will be described below in detail.

The proximal shaft 15 is preferably made from a material having a relatively high rigidity, for example, a metal such as a Ni—Ti alloy, brass, a stainless steel, or aluminum. Alternatively, a resin having a relatively high rigidity such as polyimide, polyvinyl chloride, or polycarbonate may be used as the material of the proximal shaft 15.

The main shaft portion 153 of the proximal shaft 15 is a tube having an outer diameter of about 0.3 to 3 mm, preferably, 0.5 to 1.5 mm, a wall thickness of about 10 to 150 μm, preferably, 20 to 100 μm, and a length of 300 to 2,000 mm, preferably, 700 to 1,500 mm.

The proximal shaft insertion portion 152 of the proximal shaft 15 is a tube having an outer diameter of about 0.3 to 3 mm, preferably, 0.5 to 1.5 mm, a wall thickness of about 10 to 150 μm, preferably, 20 to 100 μm, and a length of 30 to 200 mm, preferably, 50 to 180 mm.

The distal shaft 13 and the intermediate portion 14 may be formed by the same tube. Alternatively, the tube for the distal shaft 13 and the tube for the intermediate portion 14 may be separately prepared and suitably connected to each other.

With respect to the pitch of the spiral slit formed in the proximal shaft insertion portion 152, if the pitch is set to be short on the distal side and is long on the proximal side as shown in the figure, the pitch on the distal side may be in a range of 0.1 to 10 mm, preferably, 0.3 to 2 mm and the pitch on the proximal side may be in a range of 1 to 20 mm, preferably, 2 to 10 mm. The width of the spiral slit may be in a range of 1 mm or less, preferably, about 0.01 to 0.5 mm.

Examples of materials used for forming the distal shaft 13 and the intermediate portion 14 may include polymers selected from polyolefins (for example, polyethylene, polypropylene, polybutene, ethylene-propylene copolymer, ethylene-vinyl acetate copolymer, ionomer, and a mixture of at least two kinds), cross-linked polyolefins, polyvinyl chloride, polyamide, polyamide elastomer, polyester, polyester elastomer, polyurethane, polyurethane elastomer, fluoroplastic, and polyimide. These polymers may be used singly or in combination.

In particular, in the case of using the catheter of the present invention as a dilatation balloon catheter or a living organ dilatation catheter, the distal shaft 13 is preferably made from a polymer having a Shore D hardness of 70 or more and a flexural modulus of 11,000 kgf/cm$^2$ or more. It is to be noted that the optimal values of the above-described Shore hardness and the flexural modulus of the distal shaft 13 differ depending on an objective device and an objective therapy cite and are therefore not limited to those described above.

The product of the outer diameter S of the grooved portion 131 of the distal shaft 13 (see FIGS. 3 and 4) and the flexural modulus E of the material forming the distal shaft 13 may be in a range of 500 kgf/cm or more, preferably, 1,200 kgf/cm or more.

By using the above-described material suitable for the distal shaft 13 and setting the outer diameter S and the flexural modulus E as described above, the distal shaft 13 has a suitable flexural strength, to thereby enhance the pushability of the catheter having such a distal shaft 13. Concretely, in such a catheter, a pushing force applied on the proximal end of the catheter can be easily, certainly transmitted to the distal end of the catheter. In addition, since a difference in flexural strength between the grooved portion 131 and a non-grooved portion of the distal shaft 13 is optimized, it is possible to enhance the pushability of the catheter while keeping a suitable flexibility and a good kink resistance.

The distal shaft 13 and the intermediate portion 14 is a tube having an outer diameter of 0.5 to 1.5 mm, preferably, 0.7 to 1.1 mm, a wall thickness of 25 to 200 μm, preferably, 50 to 100 μm, a length of 300 to 2,000 mm, preferably, 300 to 1,500 mm.

The inner tube shaft 11 may be made from a material having a certain degree of flexibility. Examples of such materials may include polymers selected from polyolefins (for example, polyethylene, polypropylene, polybutene, ethylene-propylene copolymer, ethylene-vinyl acetate copolymer, ionomer, and a mixture of at least two kinds), cross-linked polyolefins, polyvinyl chloride, polyamide, polyamide elastomer, polyester, polyester elastomer, polyurethane, polyurethane elastomer, polyimide, and fluoroplastic. These polymers may be used singly or in combination.

The inner tube shaft 11 is a tube having an outer diameter of about 0.1 to 1.0 mm, preferably, 0.3 to 0.7 mm, a wall thickness of about 10 to 150 μm, preferably, 20 to 100 μm, and a length of 100 to 2,000 mm, preferably, 200 to 1,500 mm.

The balloon 12 may be made from a material having a certain degree of plasticity for allowing the balloon 12 to dilate a stricture of a blood vessel, for example, a polymer, silicone rubber, or latex rubber. Examples of the polymers may include polyolefins (for example, polyethylene, polypropylene, polybutene, ethylene-propylene copolymer, ethylene-vinyl acetate copolymer, and ionomer), cross-linked polyolefins, polyester such as polyethylene terephthalate, polyester elastomer, polyvinyl chloride, polyurethane, polyurethane elastomer, polyphenylene sulfide, polyamide, polyamide elastomer, and fluoroplastic. A laminated film prepared by suitably laminating layers of above polymers may be used as the material for forming balloon 12. The attachment of the balloon 12 to the distal shaft 13 may be performed by forming the balloon 12 by biaxial stretch blow molding and mounting the balloon 12 to the front side of the distal shaft 13, or integrally forming the balloon 12 on the front side of the distal shaft 13 by stretch blow molding.

In the inflated state, the balloon 12 has a cylindrical portion having an outer diameter of 1.0 to 10 mm, preferably 1.0 to 5.0 mm and a length of 5 to 50 mm, preferably 10 to 40 mm, and has the whole length of 10 to 70 mm, preferably 15 to 60 mm.

The radiopaque markers 121a and 121b are each preferably formed of a coil spring or a ring. In this embodiment, two pieces of the radiopaque makers are provided; however, one radiopaque marker or two or more radiopaque markers may be provided. The radiopaque markers 121a and 121b may be made from a material having a high radiopaque characteristic against X-rays. Examples of such materials may include Pt, W, Au, Ir, Ag, and alloys thereof.

The outer surface of the medical tube (catheter) may be covered with a lubricating material, which exhibits lubricity in a state being in contact with blood (body fluid). The lubricating material is represented by a hydrophilic polymer compound exhibiting lubricity in a wet state or silicone.

Examples of the hydrophilic polymer compounds may include methylvinylether/maleic anhydride copolymer or ester of methylvinylether/maleic anhydride copolymer, polyvinyl pyrrolidone compound, hydroxypropyl cellulose, and dimethylacrylamide-glycidyl methacrylate (DMAA-GMA).

The outer surface of the tube may be covered with such a hydrophilic polymer compound by a manner of dissolving the above hydrophilic polymer compound in a suitable solvent such as methyl ethyl ketone, acetone, tetrahydrofuran, dioxane, dimethyl formaldehyde, alcohol, or dimethyl sulfoxide, impregnating the outer surface of the tube with the solution by dipping, coating, or spraying, and removing the solvent by drying or rinsing, thereby making the hydrophilic polymer compound remain in the polymer material of the tube.

The region, to be covered with the lubricating material, of the medical tube (catheter) is not particularly limited; however, for the rapid exchange type catheter shown in FIG. 1, a region from the distal end of the catheter to the vicinity of the guide wire aperture 141 is preferably coated with the lubricating material. In particular, the provision of the lubricating coating on the grooved portion 131 is advantageous in greatly improving the sliding characteristic of the tube by combination with the effect of reducing the contact area of the outer surface of the tube with the inner surface of a lumen of a living body due to formation of the groove or grooves. Accordingly, the catheter 1 can be more smoothly advanced in a living body by eliminating interference of the irregularities of the outer surface of the grooved portion 131 with a wall of a lumen of a blood vessel or the like. In this invention, the grooved portion may have two or more grooves.

Figure 7:
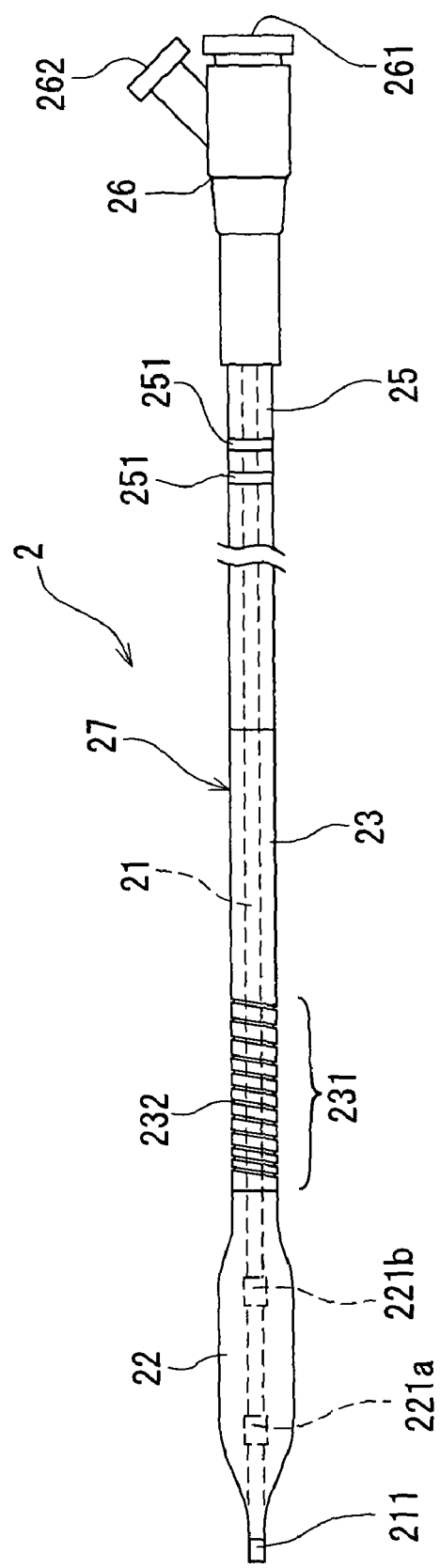
FIG. 7 is an enlarged front view of another embodiment of the catheter (medical tube) of the present invention, with parts partially omitted.
Figure 8:
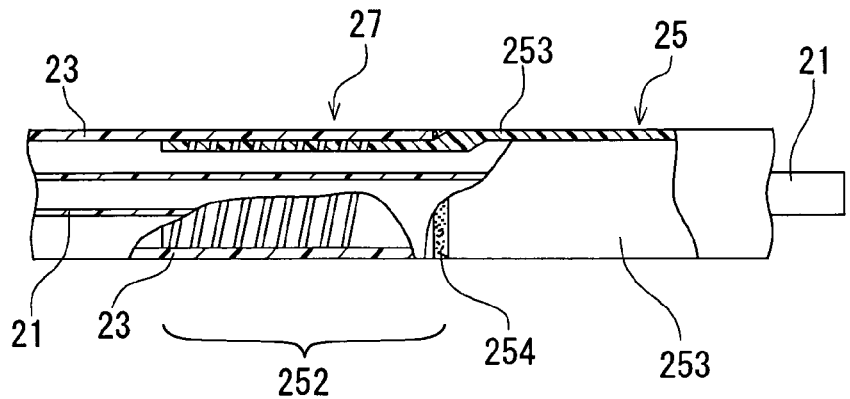
FIG. 8 is an enlarged sectional view of a connection portion between a distal shaft and a proximal shaft of the catheter shown in FIG. 7.

FIG. 7 is an enlarged front view of another embodiment of the catheter (medical tube) of the present invention, with parts partially omitted, and FIG. 8 is an enlarged sectional view showing a connection portion between a distal shaft and a proximal shaft of the catheter shown in FIG. 7. In these figures, the right side is taken as the proximal side and the left side is taken as the distal side. It is to be noted that the structure of a front portion of the catheter shown in FIG. 7 is the same as that shown in FIG. 2.

In this embodiment, the catheter of the present invention is embodied by a catheter 2 including a proximal shaft 25, a distal shaft 23 connected to a front portion of the proximal shaft 25, a hub 26 connected to the rear side of the proximal shaft 25, a balloon 22 provided at a front portion of the distal shaft 23, a balloon lumen for communicating the hub 26 to the inside of the balloon 22, and a guide wire lumen for allowing a guide wire to be inserted through the guide wire lumen, the guide wire lumen including a distal side aperture positioned on the front side from a front end of the balloon 22 and a proximal side aperture positioned on the rear side from a rear end of the balloon 22. In this catheter, at least a front portion, positioned on the rear side from the balloon 22, of the distal shaft 23 is configured as a grooved portion 231 having a groove 232. In this invention, the grooved portion may have two or more grooves.

The catheter according to the second feature of the present invention is embodied by a catheter 2 including a proximal shaft 25 having a relatively high rigidity, a distal shaft 23 provided on a front portion of the proximal shaft 25 so as to be in fluid communication with the proximal shaft 25 and having a rigidity lower than that of the proximal shaft 25, a hub 26 connected to the vicinity of a rear end of the proximal shaft 25 and configured to allow a pressure applying apparatus to be connected to the hub 26, a balloon 22 provided on a front side of the distal shaft 23 so as to be in fluid communication with the distal shaft 23 and configured to receive pressure applied from the hub 26, and a guide wire lumen for allowing a guide wire to be inserted through the guide wire lumen, the guide wire lumen including a distal side aperture positioned on the front side from a front end of the balloon 22 and a proximal side aperture positioned on the rear side from a rear end of the balloon 22. In this catheter, at least a front portion of the distal shaft 23 is configured as a grooved portion 231 having a groove 232. In this invention, the grooved portion may have two or more grooves.

The medical tube according to the third feature of the present invention is embodied by a medical tube including a tube-like shaft (outer tube shaft) 27 and a lumen formed in the outer tube shaft 27, wherein the outer rube shaft 27 includes a groove 232 formed with their depths changed in the direction toward a distal end of the medical tube. The medical tube of the present invention is usable for catheters, endoscopes, and the like. In this invention, the outer rube shaft may have two or more grooves.

A catheter 2 shown in FIG. 7 is a so-called "over-the-wire" type dilatation balloon catheter, in which a guide wire aperture is formed in a proximal portion (hub) of the catheter. As shown in FIG. 7, the catheter 2 includes an inner tube shaft 21, an outer tube shaft 27, a balloon 22, and a branch hub 26. The outer tube shaft 27 is a tubular member including a distal shaft 23 made from a relatively soft material, and a proximal shaft 25 made from a material having a rigidity higher than that of the distal shaft 23. The branch hub 26 is fixed to the rear end of the proximal shaft 25 (outer tube shaft 27).

The hub 26 has a first aperture 261 communicated to a lumen of the inner tube shaft 21 allowing a guide wire (not shown) to be inserted in the inner tube shaft 21, and a second aperture 262 having a lure taper portion connectable to a pressure applying apparatus such as an inflator. The proximal shaft 25 made from a material having a relatively high rigidity such as a metal or a hard resin is connected to the hub 26 so as to be in fluid communication with the second aperture 262. The proximal shaft 25 is provided with a depth marker 251 for easily checking the depth of the catheter 2 inserted in a guiding catheter (not shown) during angioplasty. As will be fully described later, a front portion of the proximal shaft 25 is configured as a proximal shaft insertion portion 252.

The distal shaft 23 having a relatively low rigidity, which is made from a material such as a resin, is provided on the front side of the proximal shaft 25 so as to be in fluid communication with the proximal shaft 25. A rear portion of the balloon 22 is provided on the distal side of the distal shaft 23 so as to be in fluid communication with the distal shaft 23.

The inner tube shaft 21 coaxially extends through the proximal shaft 25, the distal shaft 23 and the balloon 22. A distal end of the inner shaft 21 forms a distal tip 211. The distal tip 211 extends (projects) outwardly from a front end of the balloon 22 and is liquid-tightly connected to the front side of the balloon 22. On the other hand, a proximal end of the inner tube shaft 21 extends to the inside of the hub 26, and is liquid-tightly connected to the hub 26. A guide wire (not shown) is inserted in the inner tube shaft 21. In this case, the distal aperture of the distal tip 211 is taken as an inlet and the first aperture 261 of the hub 26 is taken as an outlet. Radiopaque markers 221a and 221b are provided at inner positions, located around the inner shaft 21, of the balloon 22.

The proximal shaft 25 is a tubular member having nearly the same outer diameter excluding the front portion as shown in FIG. 7. The diameter of a front portion 252 of the proximal shaft 25 is reduced as shown in FIG. 8. The proximal shaft 25 includes a main shaft portion 253 and the proximal shaft insertion portion 252 formed by spirally slitting the front portion of the proximal shaft 25. The outer diameter of the insertion portion 252 is nearly the same as the inner diameter of the rear portion of the distal shaft 23. The insertion portion 252 is inserted in the rear portion of the distal shaft 23.

One or two or more spiral slits are provided in the insertion portion 252 to be inserted in the distal shaft 23. The provision of the spiral slit allows the front portion 252 (insertion portion to be inserted in the distal shaft 23) of the proximal shaft 25 to be more softly curved, and also allows the insertion portion 252 to flexibly reinforce the rear portion of the distal shaft 23. Such a spiral slit can be formed by laser cutting.

With such arrangement of the proximal shaft insertion portion 252, it is possible to make an intermediate portion, that is, a connected portion between the proximal shaft 25 and the distal shaft 23 lower in rigidity (that is, softer) than the proximal shaft 25 and higher in rigidity (that is, harder) than the distal shaft 23, and hence to gradually change the rigidity of the shafts forming the catheter 2 in the direction from the proximal side to the distal side. This is advantageous in preventing, even when the intermediate portion is sharply curved, stress from being concentrated at one point, thereby reducing occurrence of kink.

The width of the spiral slit formed in the proximal shaft insertion portion 252 is determined depending on the diameter and the wall thickness of the tube and is therefore not constant. The width of the spiral slit is preferably in a range of 1.5 mm or less, more preferably, 1.0 mm or less. Also, the width of the spiral slit is preferably in a range of a half or less of the outer diameter of the insertion portion 252. As long as the spiral slit is within this range, the tube is sufficiently soft, and thereby the tube is not broken during use. If the spiral slit is arranged with the same pitch, the pitch is preferably in a range of 0.3 to 5.0 mm, especially, 0.5 to 3.0 mm. As long as the pitch of the spiral slit is within this range, the insertion portion 252 is sufficiently soft, and thereby the tube is not broken at the insertion portion 252 during use. The length of the slit portion from the distal end of the insertion portion 252 may be determined depending on the length of a blood vessel dilator.

The rear portion of the distal shaft 23 is fixed to the proximal shaft insertion portion 252 with an adhesive 254. Alternatively, the rear portion of the distal shaft 23 may be fixed to the proximal shaft insertion portion 252 by means of only a fitting force acting therebetween. In the case of bonding the rear portion of the distal shaft 23 to the proximal shaft insertion portion 252, it is preferred not to bond the front portion of the proximal shaft insertion portion 252 to the distal shaft 23, but to bond only the rear portion of the insertion portion 252 to the distal shaft 23. With this configuration, since the front portion of the insertion portion 252 is not fixed to the distal shaft 23, it is possible to more certainly deform the slit formation portion (front portion) of the insertion portion 252. It is also preferred for the slit not to be formed in the rear portion of the front portion (insertion portion) 252. With this configuration, since the slit in which the adhesive flows is not present on the proximal side, it is possible to eliminate an adhesion failure due to the lack of the adhesive flowing to the interface between the distal shaft and the proximal shaft. It is further preferred for the slit to be empty because of the absence of the flow-in of the adhesive in the slit. With this configuration, it does not prevent the slit (formed in the front portion 252) from being deformed due to the solidified adhesive.

The length of a portion with no slit from the proximal end of the insertion portion 252 is preferably in a range of about 0.5 to 250 mm, more preferably, 1.5 to 150 mm. Meanwhile, the length of the slit formation portion is preferably in a range of about 1/1.2 to 1/5 of the whole length of the front portion (insertion portion) 252.

In the example shown in FIG. 8, the pitch of the slit formed in the insertion portion 252 is nearly constant in a range from the distal side to the proximal side of the slit; however, the slit may be changed so as to be short on the distal side of the slit and long on the proximal side of the slit. This makes it possible to make the insertion portion 252 soft in the direction toward the distal end, and hence to allow the front portion to be more smoothly curved without a rapid change in physical properties.

In the catheter 2 configured as described above, when pressure is applied to the hub 26 by means of the pressure applying apparatus (not shown) connected to the hub 26, the pressure medium is transmitted from the hub 26 to the balloon 22 through the proximal shaft 25, the proximal shaft insertion portion 252, and the distal shaft 23 (balloon dilatation lumen), to dilate the balloon 22. It is to be noted that dimensions and materials of the distal shaft 23, the proximal shaft 25, the inner tube shaft 21, and the balloon 22 may be the same as those in the catheter 1 described in the previous embodiment with reference to the drawings.

As shown in FIG. 7, the front portion of the distal shaft 23 (as part of the outer tube shaft 27) is configured as a grooved portion 231. Like the grooved portion 131 shown in FIG. 1, the grooved portion 231 is formed in the front portion of the distal shaft 23, which portion is located on the proximal side from the connection portion between the distal shaft 23 and the balloon 22. The grooved portion 231 has a groove 232. In this embodiment, the groove 232 is formed into a spiral shape. The groove 232 extends in the longitudinal direction of the distal shaft 23 (catheter 2). As a result of forming the groove 232, the grooved portion 231, that is, the front portion of the distal shaft 23 becomes softer than the rear portion, provided with no groove 232, of the distal shaft 23.

In this embodiment, the grooved portion 231 is provided in a region, adjacent to the balloon 22, of the outer tube shaft 27 (distal shaft 23). Accordingly, the rigidity of the catheter 2 is smoothly changed from the portion provided with the outer tube shaft 27 (distal shaft 23) containing the inner tube shaft 21 inserted therein to the portion provided with only the balloon 22 and the inner tube shaft 21, that is, provided with no outer tube shaft 27. As a result, even if the portion, adjacent to the balloon 22, of the outer tube shaft 27 (distal shaft 23) is sharply curved in a meandering portion of a blood vessel, it is possible to prevent stress from being concentrated at one point and hence to reduce occurrence of kink. This makes it possible to certainly transmit a pushing force applied on the proximal side of the catheter 2 to the distal end of the catheter 2, and hence to insert the catheter 2 to a more peripheral vascular vessel.

The pitch and depth of the groove 232 of the grooved portion 231 and the length of the grooved portion 231 may be the same as those in the catheter 1 in the previous embodiment with reference to the drawings.

In the catheter 2 shown in the figures, the outer tube shaft 27 is divided into the distal shaft 23 and the proximal shaft 25; however, according to the present invention, the outer tube shaft 27 may be formed of the same member over the whole length. In this case, the grooved portion 231 may be provided for the entire outer tube shaft 27, and in this case, the rigidity of the catheter 2 can be more smoothly changed in the longitudinal direction by suitably changing the depth and pitch of the groove 232.

Figure 9:
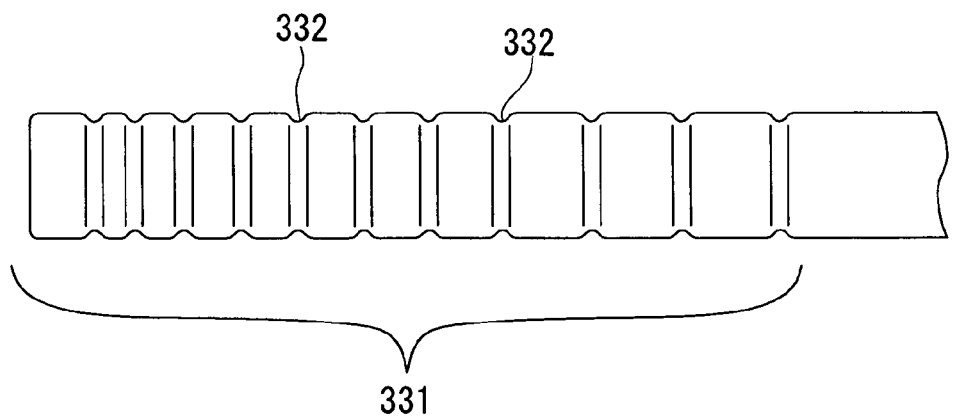
FIG. 9 is an enlarged sectional view showing another configuration example of a grooved portion.

The configuration of the groove or grooves formed in the grooved portion of the catheter of the present invention is not limited to the above-described spiral configuration. For example, the grooved portion of the catheter of the present invention may be configured as a grooved portion 331 having a plurality of annular grooves 332 shown in FIG. 9. The plurality of annular grooves 332 may be disposed so as to be spaced from each other at equal intervals; however, as shown in FIG. 9, they are preferably disposed such that a gap between adjacent grooves is narrow on the distal side of the grooved portion 331 and is wide on the proximal side of the grooved portion 331. With this configuration, the grooved portion becomes soft in the direction toward the distal end, so that the distal portion of the catheter can be smoothly curved. This is advantageous in improving the operationality of the catheter. The plurality of the annular grooves may be set to be deep on the distal side of the grooved portion, shallow on the proximal side of the grooved portion, and middle on the intermediate region of the grooved portion. Like the example shown in FIG. 6, the depths of the groove may be set to be deepest on the distal side and to become gradually or stepwise shallower in the direction toward the proximal side.

The pitch, depth of the annular grooves 332 of the grooved portion 331 and the length of the grooved portion 331 may be the same as those in the catheter 1 described in the previous embodiment with reference to the drawings.

In the embodiment shown in the figures, the outer diameter of the distal shaft (outer tube shaft) of the grooved portion is set to be constant; however, the present invention is not limited thereto but may be configured such that the outer diameter of the distal shaft of the grooved portion may be changed. In particular, by forming grooves in the distal shaft while reducing the outer diameter of the distal shaft in the direction toward the distal end, the rigidity of the catheter (medical tube) can be more smoothly changed in the longitudinal direction of the catheter (medical tube).

The formation of the above-described grooved portion may be made by forming a groove or grooves in the outer surface of the distal shaft (outer tube shaft) by mechanical cutting, laser cutting, or the like. In the case of forming a grooved portion having spiral groove, according to this embodiment, the spiral groove can be formed in accordance with the following method.

First, a core member having an outer diameter nearly equal to an inner diameter of a shaft to be grooved is placed in the shaft. The core member may be selected from metal wires such as a copper wire and a stainless steel wire, and hard plastic wires. If the shaft is produced by covering a wire (for example, a copper wire) with a plastic material by extrusion molding, the wire may be used as the core member.

The shaft is displaced in the longitudinal direction while being rotated in the circumferential direction, and simultaneously a fine wire made from a metal such as stainless steel, tungsten, gold, or a copper is fed from a fine wire supply unit (not shown) to the shaft with a tension applied to the fine wire in the direction perpendicular to the longitudinal direction of the shaft. The fine wire is thus spirally wound around the outer surface of the shaft while digging into the shaft. As a result, portions, around which the fine wire has been wound, of the shaft are depressed, to form spiral groove.

In this method, the pitch of the fine wire spirally wound around the shaft is changed by changing the displacement speed of the shaft in the longitudinal direction, to change the pitch of the spiral groove. Also, the digging depth of the fine wire in the shaft is changed by changing a tension applied to the fine wire, to change the depth of the spiral groove.

The cross-sectional shape of the fine wire may be any other shape, for example, a round shape, an elliptic shape, a square shape, or a parallelogram shape. The outer diameter of the fine wire depends on the width of the groove of a grooved portion to be produced; however, in the case of using the fine wire having a circular cross-section, the outer diameter of the fine wire is preferably in a range of 20 to 100 μm, more preferably, 40 to 80 μm.

After the fine wire is wound around the shaft over a specific length, the rotation and the longitudinal displacement (movement) of the shaft are stopped, and the shaft is rotated in the reverse direction, to thereby easily remove the fine wire from the shaft. After the rotation of the shaft is stopped, the core member is pulled out of the shaft, to thus accomplish the shaft having the grooved portion.

EXAMPLE

A nylon tube (Shore D hardness: 72, flexural modulus: 11,175 kgf/cm$^2$) having an outer diameter of 0.9 mm and a wall thickness of 85 μm was formed by covering a copper wire with nylon by extrusion molding, to produce a distal shaft. A spiral groove was then formed in the distal shaft by the following spiral groove forming process. In this process, the copper wire used for extrusion molding was used as a core member.

Both ends of the distal shaft were chucked, and one end of a metal fine wire (material; tungsten) having an outer diameter of 60 μm was fixed in the vicinity of the distal shaft. The distal shaft was rotated at a rotational speed of 300 rpm in the circumferential direction and simultaneously displaced at a movement speed of 60 mm/min in the longitudinal direction. In such a state, the fine wire was fed from a fine wire supply unit with a tension applied thereto in the direction perpendicular to the longitudinal direction of the shaft, to be wound around the distal shaft. After that, the circumferential rotation and the longitudinal movement of the distal shaft were stopped, and the distal shaft was rotated in the reverse direction, to remove the fine wire from the shaft. After the rotation of the shaft was stopped, the core member was pulled out of the shaft, to produce the distal shaft having a spiral groove.

The above-described process was repeated except that the tension applied to the fine wire was variously altered, to produced five kinds of distal shafts each having a length of 150 mm: a distal shaft in Example 1 (depth of a spiral groove: 35 μm); a distal shaft in Example 2 (depth of a spiral groove: 43 μm); a distal shaft in Example 3 (depth of a spiral groove:

50 µm); a distal shaft in Example 4 (depth of a spiral groove: 57 µm); and a distal shaft in Example 5 (depth of a spiral groove: 60 µm).

The above process was further repeated except that the tension applied to the fine wire wound around the distal shaft was stepwise changed during the process, to produce a distal shaft (Example 6). In this distal shaft having the whole length of 200 mm, a front portion having a length of 100 mm was grooved, wherein in a first region from the distal end (of the grooved portion) to a point of 10 mm in length apart from the distal end, the depth of a groove was changed at a constant rate from 0 µm to 50 µm in the direction toward the proximal end; in a second region from points of 10 mm to 80 mm in length apart from the distal end, the depth of the groove was kept at a constant value of 50 µm; and in a third region from points of 80 mm to 100 mm in length apart from the distal end, the depth of the groove was changed at a constant rate from 50 µm to 0 µm in the direction toward the proximal end.

(Experiment)

Figure 10:
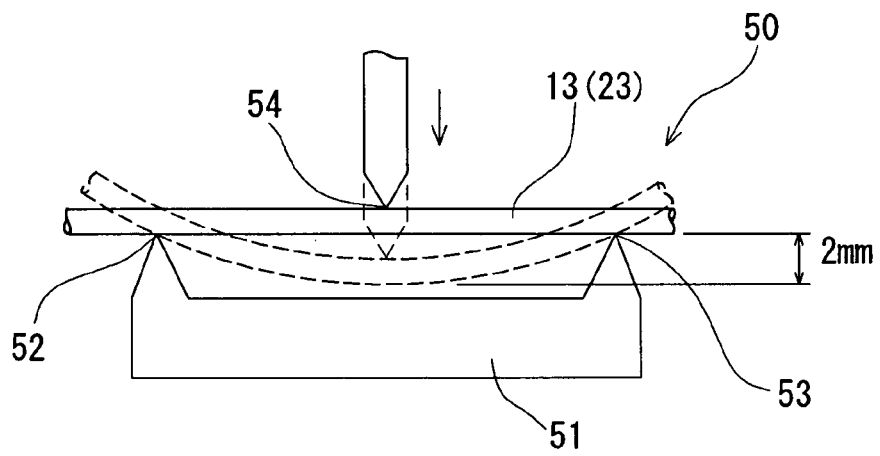
FIG. 10 is a front view showing an experimental apparatus and an experimental method in an example of the present invention.

The rigidity of each of the distal shafts in Examples 1 to 5 was examined by measuring the flexural strength of the distal shaft using a jig 50 shown in FIG. 10. A grooved portion of the distal shaft 13 (23) was placed on both edges 52 and 53 of a base 51. The distance between the edges 52 and 53 was set to one inch. A portion, located at an intermediate portion between the edges 52 and 53, of the distal shaft was depressed downwardly for a depth of 2 mm by an edge 54, and a load applied to the edge 54 was measured. The depressing speed of the edge 54 was set to 5 mm/min. The measurement was performed at room temperature (20° C.). The results are shown in Table 1.

TABLE 1

|  | groove depth (µm) | flexural strength (gf) |
| --- | --- | --- |
| Example 1 | 35 | 9.0 |
| Example 2 | 43 | 7.5 |
| Example 3 | 50 | 6.5 |
| Example 4 | 57 | 6.0 |
| Example 5 | 60 | 5.5 |

As is apparent from these results, in the distal shaft (groove depth: 35 µm), the ratio of the groove depth to the wall thickness of the distal shaft is about 40% and the flexural strength is 9 gf; and in the distal shaft (groove depth: 60 µm), the ratio of the groove depth to the wall thickness of the distal shaft is about 70%, and the flexural strength is 5.5 gf. Accordingly, it becomes apparent that the flexural strength can be changed by controlling the groove depth.

As described above, the catheter of the present invention is advantageous in being excellent in pushability, trackability, torque transmission performance, and kink resistance, and having flexibility at the front portion of the catheter, and is also advantageous in being capable of suppressing occurrence of kink, thereby reaching a more peripheral target cite of a living body because the distal shaft has no rapid change point of rigidity and exhibits the rigidity (physical property) smoothly changed in the longitudinal direction. In particular, the balloon catheter of the present invention is advantageous in being capable of suppressing occurrence of kink in a front portion, adjacent to a balloon, of a shaft main body, thereby smoothly reaching a more peripheral vascular vessel.

The medical tube of the present invention includes a tube-like outer tube shaft, and a lumen formed in the outer tube shaft, wherein the outer tube shaft has a groove formed with their depths changed in the direction toward the distal end of the medical tube.

Accordingly, the medical tube of the present invention is advantageous in being excellent in pushability, trackability, torque transmission performance, and kink resistance, and having a flexibility at the distal portion of the tube, and is also advantageous in being capable of suppressing occurrence of kink, thereby reaching a more peripheral target cite of a living body because the outer tube shaft has no rapid change point of rigidity and exhibits the rigidity (physical property) smoothly changed in the longitudinal direction.

The catheter and the medical tube of the present invention have a further advantage that since the rigidity (physical property) can be more smoothly changed by changing the pitch and depth of a groove in the longitudinal direction of a grooved portion or combining the changes in pitch and depth of the groove with each other, each of the catheter and the medical tube is capable of significantly suppressing occurrence of kink, thereby easily reaching a more peripheral vascular vessel.

In addition, according to the present invention, the steps of producing each of the catheter and the medical tube are simpler than the prior art steps of connecting shafts having different rigidities or changing the wall thickness or outer diameter of the shaft by extrusion molding.

While the preferred embodiments of the present invention have been described using specific terms, such description is for illustrative purposes only, and it is to be understood that changes and variations may be made without departing from the spirit or scope of the following claims.

What is claimed is:

1. A catheter comprising:
   a proximal shaft;
   an intermediate member connected to a front side of said proximal shaft;
   a distal shaft connected to a front portion of said intermediate member;
   a hub provided to a rear side of said proximal shaft;
   a balloon connected at a front portion of said distal shaft;
   an inner tube shaft coaxially extends through said distal shaft and said balloon and connected to a distal end of said balloon;
   a balloon lumen for communicating said hub to the inside of said balloon; and
   a guide wire lumen for allowing a guide wire to be inserted through said guide wire lumen, said guide wire lumen including a distal side aperture positioned on the distal side from a front end of said balloon and a proximal side aperture formed in a side surface of said intermediate member;
   a front portion of said distal shaft is configured as a grooved portion having a groove, the front portion of said distal shaft having the groove being positioned on a rear side of said balloon;
   a rear portion of said distal shaft is free of grooves;
   wherein said grooved portion is provided at a portion adjacent to said balloon and extends toward a proximal side of said distal shaft;
   said groove possessing a depth which changes relative to a longitudinal extent of the distal shaft so as to be relatively larger on a distal side of said grooved portion and relatively smaller on a proximal side of said grooved portion; and
   said proximal shaft includes a main shaft portion and a proximal shaft insertion portion formed by spiral slit on a front portion of said proximal shaft and inserted into a rear portion of said intermediate member, and a pitch of said spiral slit becomes gradually shorter toward a distal end of said spiral slit.

2. A catheter according to claim 1, wherein said groove is formed into spiral shape or annular shape.

3. A catheter according to claim 2, wherein the pitch of said spiral or annular groove is changed in the direction toward the distal end of said catheter.

4. A catheter according to claim 1, wherein the depth of said groove is in a range of 30 to 90% of the wall thickness of said distal shaft.

5. A catheter according to claim 1, wherein said grooved portion includes a first region, a second region, and a third region disposed in this order from the distal side, and the depth of said groove in said second region is larger than that of said groove in said third region and the depth of said groove in said first region is larger than that of said groove in said second region.

6. A catheter according to claim 1, wherein said distal shaft is made from a polymer material having a Shore D hardness of 70 or more and a flexural modulus of 11,000 kgf/cm2 or more.

7. A catheter according to claim 1, wherein the product of an outer diameter (S) of said distal shaft of said grooved portion and a flexural modulus (E) of a material forming said distal shaft is in a range of 500 kgf/cm or more.

8. A catheter according to claim 1, wherein said distal shaft has a distal portion and a proximal portion, and the rigidity of said proximal portion of said distal shaft is lower than that of said proximal shaft and is higher than that of said distal portion of said distal shaft.

9. A catheter according to claim 1, wherein said groove is formed in an outer surface of said distal shaft.

10. A catheter comprising:
a proximal shaft;
an intermediate member connected to a front side of said proximal shaft;
a distal shaft connected to a front portion of said intermediate member;
a hub provided to a rear side of said proximal shaft;
a balloon connected at a front portion of said distal shaft;
an inner tube shaft coaxially extends through said distal shaft and said balloon and connected to a distal end of said balloon;
a balloon lumen for communicating said hub to the inside of said balloon;
a guide wire lumen for allowing a guide wire to be inserted through said guide wire lumen, said guide wire lumen including a distal side aperture positioned on the distal side from a front end of said balloon and a proximal side aperture formed in a side surface of said intermediate member;
a front portion of said distal shaft is configured as a grooved portion having a groove, the front portion of said distal shaft having the groove being positioned on a rear side of said balloon;
a rear portion of said distal shaft is free of grooves;
wherein said grooved portion is provided at a portion adjacent to said balloon and extends toward a proximal side of said distal shaft;
said groove has a depth in a range of 30 to 90% of a wall thickness of said distal shaft,
said groove possessing a depth which changes relative to a longitudinal extent of the distal shaft so as to be relatively larger on a distal side of said grooved portion and relatively smaller on a proximal side of said grooved portion; and
said proximal shaft includes a main shaft portion and a proximal shaft insertion portion formed by spiral slit on a front portion of said proximal shaft and inserted into a rear portion of said intermediate member, and a pitch of said spiral slit becomes gradually shorter toward a distal end of said spiral slit.

11. A catheter comprising:
a proximal shaft;
an intermediate member connected to a front side of said proximal shaft;
a distal shaft connected to a front portion of said intermediate member;
a hub provided to a rear side of said proximal shaft;
a balloon connected at a front portion of said distal shaft;
an inner tube shaft coaxially extends through said distal shaft and said balloon and connected to a distal end of said balloon,
a balloon lumen for communicating said hub to the inside of said balloon; and
a guide wire lumen for allowing a guide wire to be inserted through said guide wire lumen, said guide wire lumen including a distal side aperture positioned on the distal side from a front end of said balloon and a proximal side aperture formed in a side surface of said intermediate member; wherein
a front portion, positioned on a rear side from said balloon, of said distal shaft is configured as a grooved portion having a groove;
a rear portion of said distal shaft is free of grooves;
wherein said grooved portion is provided at a portion adjacent to said balloon and extends toward a proximal side of said distal shaft; and
said proximal shaft includes a main shaft portion and a proximal shaft insertion portion formed by spiral slit on a front portion of said proximal shaft and inserted into a rear portion of said intermediate member, and a pitch of said spiral slit becomes gradually shorter toward a distal end of said spiral slit.

* * * * *